(12) United States Patent
Lao (10) Patent No.: US 7,255,994 B2
(45) Date of Patent: Aug. 14, 2007

(54) LIGATION ASSAY

(75) Inventor: Kai Qin Lao, Pleasanton, CA (US)

(73) Assignee: Applera Corporation, Foster City, CA (US)

( * ) Notice: Subject to any disclaimer, the term of this patent is extended or adjusted under 35 U.S.C. 154(b) by 397 days.

(21) Appl. No.: 10/866,012

(22) Filed: Jun. 10, 2004

(65) Prior Publication Data

US 2005/0064459 A1    Mar. 24, 2005

Related U.S. Application Data

(60) Provisional application No. 60/477,614, filed on Jun. 10, 2003.

(51) Int. Cl.
 C12Q 1/68     (2006.01)
 C12P 19/34    (2006.01)
 C07H 21/02    (2006.01)
 C07H 21/04    (2006.01)

(52) U.S. Cl. .................. 435/6; 435/91.2; 536/23.1; 536/24.3

(58) Field of Classification Search .............. 435/6; 536/23.1, 24.3
 See application file for complete search history.

(56) References Cited

U.S. PATENT DOCUMENTS 5,674,679 A * 10/1997 Fuller .......................... 435/6
5,854,033 A * 12/1998 Lizardi ....................... 435/91.2
2002/0150921 A1   10/2002 Barany et al.
2004/0029142 A1 *  2/2004 Schon ........................... 435/6
2004/0058330 A1 *  3/2004 Aevarsson et al. ............ 435/6
2004/0110134 A1 *  6/2004 Wenz et al. .................... 435/6
2006/0141475 A1 *  6/2006 Rosenblum et al. ........... 435/6

FOREIGN PATENT DOCUMENTS

| EP | 1 130 113 A1 | 2/2000 |
| WO | WO97/04128 | 2/1997 |
| WO | WO 02/053778 A2 | 7/2002 |
| WO | WO 03/002762 A2 | 1/2003 |

OTHER PUBLICATIONS

Zhang et al., Whole genome amplification from a single cell: Implications for genetic analysis. PNAS 89 : 5847-5851 (1992).*
International Preliminary Report and Written Opinion dated Dec. 13, 2005, issued in International Application No. PCT/US2004/018396, 7 pages.

* cited by examiner

Primary Examiner—Ethan Whisenant
(74) Attorney, Agent, or Firm—Andrew K. Finn (57) ABSTRACT

Disclosed are methods and kits for detecting or quantifying one or more target polynucleotide sequences in a sample. Embodiments of the invention employ a first ligation reaction, a subsequent optional amplification reaction, and a second ligation reaction. Embodiments of the invention combine the specificity of both hybridization and ligation reactions along with universal probe polynucleotide sequences to achieve specific and multiplexed detection of a plurality of target polynucleotide sequences.

18 Claims, 3 Drawing Sheets

LIGATION ASSAY

CROSS REFERENCE TO RELATED APPLICATIONS

This application claims the benefit of priority to U.S. Provisional Application No. 60/477,614, filed on Jun. 10, 2003, which is hereby incorporated in its entirety by reference.

FIELD OF INVENTION

The invention is in the field of molecular biology.

REFERENCES

Ausubel et al., eds., *Current Protocols in Molecular Biology Vol.* 1, Chapter 2, Section I, John Wiley & Sons, New York (1993).
Fasman, 1989, Practical Handbook of Biochemistry and Molecular Biology, pp. 385-394, CRC Press, Boca Raton, Fla.
Boom et al., U.S. Pat. No. 5,234,809.
Walsh et al., *Biotechniques* 10(4): 506-513 (1991).
Miller et al., *Nucleic Acids Res.* 16(3):9-10 (1988).
Mullis et al., eds, *The Polymerase Chain Reaction*, BirkHauser, Boston, Mass. (1994).
Lizardi et al., U.S. Pat. No. 6,124,120
Lao et al., U.S. patent application Ser. No.10/151061
Birkenmeyer, et al., J. Virological Methods 35: 117-126 (1991).
Landregren, Trends in Genetics 9: 199-202 (1993).
Bi et al., U.S. Pat. No. 6,511,810
Mouritzen et al., 2003 Expert Rev. Mol. Diagn. 3(1), (2003)
Chen et al., U.S. Pat. No. 6,469,151
Christensen and Pedersen, 2002, Nucleic Acids Research 30:22:4918-4925
Eragen, U.S. Pat. No. 5,432,272
Beaucage and Iyer, *Tetrahedron* 48:2223-2311 (1992).
Gait, M. J., ed., *Oligonucleotide Synthesis: A Practical Approach*, IRL Press, Oxford, (1984 and 1990 editions).
Grossman et al., U.S. Pat. No. 5,514,543
Grossman et al., U.S. Pat. No. 5,470,705
Grossman et al., U.S. Pat. No. 5,580,732
Woo et al., U.S. Pat. No. 09/836704
Xu et a., 2003 Nucleic Acids Research, 31: 8: e43
Haugland, *Handbook of Fluorescent Probes and Research Chemicals*, Molecular Probes, Inc., Eugene, Oreg. (1992).
Hermanson, G. T. Bioconjugate Techniques, Academic Press, San Diego, Calif. (1996).
Beaucage, S. L. Current Protocols in Nucleic Acid Chemistry, John Wiley and Sons, New York, N.Y. (2000)
Matthews et al, *Anal. Biochem.* 169:1-25 (1988).
Keller and Manak, *DNA Probes,* 2nd Ed., Stockton Press, New York (1993).
Eckstein, F., *Oligonucleotides and Analogs: A Practical Approach*, Chapters 8 and 9, IRL Press, Oxford, GB (1991).
Kricka, L. J., ed., *Nonisotopic DNA Probe Techniques*, Academic Press, Inc., New York (1992).
Fung et al, U.S. Pat. No. 4,757,141.
Hobbs, Jr., et al., U.S. Pat. No. 5,151,507.
Menchen et al., PCT Publication No. WO 94/05688 (1994).
Menchen et al., U.S. Pat. No. 5,188,934.
Bergot et al., PCT Application No. PCT/US90/05565 (WO 91/07507).
Rosenblum et al., *Nucl. Acids Res.* 25:4500-4504 (1997).
U.S. Pat. No. 5,185,243
EP Application 32038
EP Application 439182
PCT Publication No. WO 90/01069
Liu and Sommer, Nucleic Acids Res. 2002 Jan. 15;30(2): 598-604.
Barany et al., U.S. Pat. No. 5,830,711
Backman and Wang, U.S. Pat. No. 320308 B1
Barany et al., U.S. patent application 9925437
Letsinger and Gryaznov U.S. Pat. No. 5,476,930
Gryanznov et al., U.S. Pat. No. 5,741,643
Kool et al., Nature Biotechnology, Vol. 19, 148-152
Royer et al., EP Patent 324616 B1
Barany et al., U.S. Pat. No. 6,027,889
Barany et al., U.S. Pat. No. 5,494,810
Grossman, P. D., and Colbum, J. C., eds., *Capillpary Electrophoresis: Theory and Practice*, Academic Press, Inc., New York (1992).
Schena, M., et al., *Science* 270:467 (1995).
Shalon, D., Ph.D. Dissertation, Falconer Library, Stanford University, California (1995).
Pon et al., *Biotechniques* 6:768-775 (1988).
Barany et al., PCT Application No. PCT/US91/06103.
Fodor, S. P. A., et al., *Science* 251:767 (1991).
Fodor, S. P. A., et al., U.S. Pat. No. 5,445,934 (1995).
Pirrung et al., U.S. Pat. No. 5,143,854.
Shoemaker et al., European Pub. No. EP 799,897 A1 (1997).
Barrett, R. W., et al., U.S. Pat. No. 5,482,867 (1996).
Brenner, PCT Publications No. WO 96/12014 and WO 96/41011.
Albretsen et al., *Anal. Biochem.* 189:40 (1990).
Khrapko, K. R., et al., *DNA Seguencing* 1:375 (1991).
Ji et al., *Anal. Chem.* 65:1323-1328 (1993).
Cantor et al, U.S. Pat. No. 5,482,836.
Breslauer et al., *Proc. Natl. Acad. Sci.* 83:3746-3750 (1986).
Wetmur, *Crit. Rev. Biochem. Mol. Biol.* 26:227-259 (1991).
Mathies, R. A., et al., U.S. Pat. No. 5,091,652 (1992).
Ploem, J. S., in *Fluorescent and Luminescent Probes for Biological Activity*, Mason, T. W., Ed., Academic Press, London, pp. 1-11 (1993).
Yershov, G., et al., *Proc. Natl. Acad. Sci.* 93:4913 (1996).
Johnston, R. F., et al., *Electrophoresis* 11:355 (1990).
Drmanac, R., et al., *Electrophoresis* 13:566 (1992).
Drmanac, R., et al., *Science* 260:1649 (1993).

Introduction

Methods for detection and analysis of target nucleic acid sequences have found wide utility in basic research, clinical diagnostics, forensics, and other areas. One important use is in the area of genetic polymorphism analysis. Genetic polymorphisms generally concern the genetic sequence variations that exist among homologous loci from different members of a species. Genetic polymorphisms can arise through the mutation of genetic loci by a variety of processes, such as errors in DNA replication or repair, genetic recombination, spontaneous mutations, transpositions, etc. Such mutations can result in single or multiple base substitutions, deletions, or insertions, as well as transpositions, duplications, etc.

Single base substitutions (transitions and transversions) within gene sequences can cause missense mutations and nonsense mutations. In missense mutations, an amino acid residue is replaced by a different amino acid residue, whereas in nonsense mutations, stop codons are created that lead to truncated polypeptide products. Mutations that occur within signal sequences, e.g., for directing exon/intron splicing of mRNAs, can produce defective splice variants with dramatically altered protein sequences. Deletions, insertions, and other mutations can also cause frameshifts in which contiguous residues encoded downstream of the mutation are replaced with entirely different amino acid residues. Mutations outside of exons can interfere with gene expression and other processes.

Genetic mutations underlie many disease states and disorders. Some diseases have been traced directly to single point mutations in genomic sequences (e.g., the A to T mutation associated with sickle cell anemia), while others have been correlated with large numbers of different possible polymorphisms located in the same or different genetic loci (e.g., cystic fibrosis). Mutations within the same genetic locus can produce different diseases (e.g., hemoglobinopathies). In other cases, the presence of a mutation may indicate susceptibility to particular condition for a disease but is insufficient to reliably predict the occurrence of the disease with certainty. Many known mutations have been localized to gene-coding sequences, splice signals, and regulatory sequences. However, it is expected that mutations in other types of sequences can also lead to deleterious, or sometimes beneficial, effects. Genetic variations may also be used as markers for genetic mapping studies.

The large number of potential genetic polymorphisms poses a significant challenge to the development of methods for identifying and characterizing nucleic acid samples and for diagnosing and predicting disease. In other applications, it is desirable to detect the presence of pathogens or exogenous nucleic acids and to detect or quantify RNA transcript levels.

In light of the increasing amount of sequence data that is becoming available for various organisms, and particularly for higher organisms such as humans, there is a need for rapid and convenient methods for determining the presence or absence of target mutations. Ideally; such a method should have high sensitivity, accuracy, and reproducibility. Also, the method should allow simultaneous detection of multiple target sequences in a single reaction mixture.

SUMMARY

In one aspect, the invention provides a method for identifying one or more target nucleotide sequences. The method comprises performing a first reaction, wherein a target sequence is hybridized to a primary probe set and the primary probe set is ligated together, thereby forming one or more first ligation products. The one or more first ligation products further comprises a tag sequence that is not complementary to the target. Thereafter, a second reaction is performed, wherein the tag sequence of the first reaction product is hybridized to a secondary probe set and the secondary probe set is ligated together. The product of the second ligation reaction is then detected and the identity of the target nucleotide sequence determined therefrom.

In another aspect, the invention provides a method for identifying one or more target nucleotide sequences. The method comprises mixing a sample comprising a target nucleotide sequence with a primary probe set. The primary probe set comprises one or more first primary probes and a second primary probe. The one or more first primary probes comprise a target specific portion, a target-identifying portion, and a primer portion. The target specific portions of the one or more first primary probes differ by at least one base. The second primary probe comprises a locus specific portion and a primer portion. The one or more first primary probes are suitable for ligation with the second primary probe when hybridized adjacent to one another on the target nucleotide sequence, thereby forming a first ligase detection reaction mixture.

Following the formation of the first ligase detection reaction mixture, one or more ligation detection reaction cycles are performed to form a first ligation product. The first ligation product comprises the upstream primer portion, the target-identifying portion, the target-specific portion and the locus-specific portion ligated together, and the downstream primer portion. The first ligation product is then optionally amplified to form an amplification product.

Following the optional amplification of the first ligation product, the amplification product is then mixed with a secondary probe set. The secondary probe set comprises one or more first secondary probes, and a second secondary probe. The one or more first secondary probes comprise a primer portion. The second secondary probe comprises a target-identifying portion. The one or more first secondary probes are suitable for ligation with the second secondary probe when hybridized adjacent to one another on the amplification product, thereby forming a second ligase detection reaction mixture.

Following formation of the second ligase detection reaction mixture, one or more ligase detection reaction cycles are performed to form a second ligation product. The one or more second ligation products comprise the primer portion of the one or more first secondary probes ligated to the target identifying portion of the second secondary probe.

In one embodiment, the one or more first probes of the primary probe set further comprise the same target identifying portion and a different primer portion.

In another embodiment, an optional amplification of the one or more first ligation products is performed. In another embodiment, an optional amplification of the one or more second ligation products is performed. In another embodiment, an optional amplification of both the one or more first ligation products and the one or more second ligation products is performed.

In another embodiment, the ligation products of the second ligation detection reaction are separated and identification of the target nucleotide sequence achieved by the distinct primer portion and target-identifying portion of the second ligation product.

In a further embodiment, the second probe of the secondary probe set further comprises a mobility modifying moiety, wherein separating the ligation products of the second ligation detection reaction further comprises a mobility-dependent analysis technique. The identity of the target nucleic acid is achieved by the distinct mobility of the ligation products of the second ligation detection reaction.

In a yet further embodiment, the mobility dependent analysis technique further comprises capillary electrophoresis.

In one embodiment, one of the probes further comprises a label.

In a further embodiment, the target identity is ascertained by hybridization of the target identifying portion to an array.

In one embodiment, the relative amounts of a plurality of targets are compared between two or more samples.

In a further embodiment, the plurality of targets further comprises expressed genes, the two or more samples are initially in separate reactions, and each sample is mixed with a primary probe set.

In a yet further embodiment, the expressed genes are amplified and converted into cDNA.

In a further embodiment, mutation profiling is performed in tumor samples.

In one embodiment, removal of unincorporated reaction components is achieved with affinity moiety pull-out.

In a further embodiment, the affinity moiety pull-out further comprises biotin-streptavidin.

In one embodiment, removal of unincorporated reaction components is achieved with enzymatic degradation.

In one embodiment, the target nucleotide sequences are initially amplified by a whole genome amplification procedure.

In another embodiment, the target nucleotide sequences are initially amplified by a partial genome amplification procedure.

DETAILED DESCRIPTION OF THE INVENTION

The present invention provides methods for detecting or quantifying one or more selected target nucleotide sequences in a sample. A highly specific ligase enzyme is employed in a first ligation reaction to ligate together a primary probe set that is complementary to a target polynucleotide sequence. The highly specific ligase enzyme is then employed in a second ligation reaction to ligate together a secondary probe set that is complementary to sequence information that was introduced by the primary probe set in the first ligation reaction. The invention is highly accurate, permitting detection of target sequences with high specificity. Because the product of the first ligation reaction, the second ligation reaction, or both, are amplified, the method is also highly sensitive, allowing detection and/or quantitation of small amounts of target sequences. The invention is advantageous for a variety of applications, including, without limitation, genotyping, detection of genetic polymorphisms, detection of genetic mutations, detection of gene expression differences, and detection of genomic methylation patterns.

Definitions

As used herein, "target polynucleotide sequence" refers to a sequence of interest. The target polynucleotide sequence serves as a template for a ligation reaction. Target polynucleotides include, but are not limited to, genomic DNA, including mitochondrial DNA and nucleolar DNA, cDNA, synthetic DNA, plasmid DNA, yeast artificial chromosomal DNA (YAC), bacterial artificial chromosomal DNA (BAC), and other extrachromosomal DNA. Target nucleic acid templates also include, but are not limited to, RNA, synthetic RNA, mRNA, tRNA, and analogs of both RNA and DNA, such as peptide nucleic acids (PNA).

The term "nucleic acid" or "polynucleotide" refers to a linear polymeric chain of nucleotide monomer units that are covalently connected to one another by phosphate ester internucleoside linkages. The nucleotide monomer units may comprise any of the nucleotides described herein, including, but not limited to, specific nucleotides, nucleotide analogs, and universal nucleotides. Unless stated otherwise, "nucleic acid" or "polynucleotide" as used herein encompass polymers of any length, including oligonucleotides, polynucleotides, and nucleic acids as those terms are commonly used in the art. Thus, where polynucleotides of specific size ranges are intended, the number of monomer units is specifically delineated. In certain embodiments, polynucleotides according to the invention can range in size from a few monomer units (e.g., 4 to 40), to several hundreds of monomer units, to several thousands of monomer units, or even more monomer units. Whenever a polynucleotide is represented by a sequence of letters, e.g., "ATGCCTG," it will be understood that the sequence is presented in the 5' to 3' direction.

As used herein, the term "primary probe set" refers to one or more nucleic acids or nucleic acid analogs that can be used in the first ligation reaction, wherein each probe can hybridize, via hydrogen binding, to a target polynucleotide with sequence specificity, thereby introducing a tag sequence in such fashion that is suitable for the purposes of this invention.

As used herein, the term "secondary probe set" refers to one or more nucleic acids or nucleic acid analogs that can be used in the second ligation reaction, wherein each probe can hybridize, via hydrogen binding, to the tag portion of the product of the first ligation reaction with sequence specificity, in such fashion that is suitable for the purposes of this invention.

As used herein, the term "interrogator base" refers to one or more nucleotides that vary between the target specific portion of the one of more first probes of the primary probe set. The location of the interrogator base may be throughout the polynucleotide sequence. In certain embodiments, the interrogator base is located at the 3' end position of the target specific portion of first primary probes. In other embodiments, the interrogator base is located at the penultimate base of the 3' position of the target specific portion of the first primary probes. In other embodiments, the interrogator base is located in the more 5' areas of the target specific portion of the first primary probes. In certain embodiments, the interrogator base is located at the 5' end position of the target specific portion of the second primary probes. In certain embodiments, the interrogator base is located at the penultimate base of the 5' end of the target specific portion of the second primary probes. In other embodiments, the interrogator base is located in the more 5' areas of the target specific portion of the second primary probes.

The term "primer" as used herein refers to a polynucleotide sequence, whether natural or synthetic, that is capable of acting as a point of initiation of nucleic acid synthesis under conditions in which primer extension is initiated. The appropriate length of a primer depends on the intended us of the primer, but typically ranges from 15 to 35 nucleotides. Short primer molecules generally require cooler temperatures to form sufficiently stable hybrid complexes with the template. A primer need not reflect the exact sequence of the template but must be sufficiently complementary to hybridize with a template for primer elongation to occur.

The term "template" as used herein, includes target nucleic acid templates and ligation products. A template is a nucleic acid molecule that serves as a template for a ligation reaction.

As used herein, "mobility-dependent analysis technique" or MDAT means an analytical technique based on differential rates of migration between different analyte species. Exemplary mobility-dependent analysis techniques include electrophoresis, chromatography, mass spectroscopy, sedimentation, e.g., gradient centrifugation, field-flow fractionation, multi-stage extraction techniques, and the like.

The term "nucleotide" as used herein generically encompasses the following terms, which are defined below: nucleotide base, nucleoside, and nucleotide analog.

The term "nucleotide base", as used herein, refers to a substituted or unsubstituted parent aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, purines such as 2-aminopurine, 2,6-diaminopurine, adenine (A), ethenoadenine, N6-Δ2-isopentenyladenine (6iA), N6-Δ2-isopentenyl-2-methylthioadenine (2ms6iA), N6-methyladenine, guanine (G), isoguanine, N2-dimethylguanine (dmG), 7-methylguanine (7 mG), 2-thiopyrimidine, 6-thioguanine (6sG) hypoxanthine and O6-methylguanine; 7-deaza-purines such as 7-deazaadenine (7-deaza-A) and 7-deazaguanine (7-deaza-G); pyrimidines such as cytosine (C), 5-propynylcytosine, isocytosine, thymine (T), 4-thiothymine (4sT), 5,6-dihydrothymine, O4-methylthymine, uracil (U), 4-thiouracil (4sU) and 5,6-dihydrouracil (dihydrouracil; D); indoles such as nitroindole and 4-methylindole; pyrroles such as nitropyrrole; nebularine; base (Y); etc. In certain embodiments, nucleotide bases are universal nucleotide bases. Additional exemplary nucleotide bases can be found, e.g., in Fasman, 1989, Practical Handbook of Biochemistry and Molecular Biology, pp. 385-394, CRC Press, Boca Raton, Fla., and the references cited therein.

The term "nucleoside", as used herein, refers to a compound having a nucleotide base covalently linked to the C-1' carbon of a pentose sugar. In certain embodiments, the linkage is via a heteroaromatic ring nitrogen. Typical pentose sugars include, but are not limited to, those pentoses in which one or more of the carbon atoms are each independently substituted with one or more of the same or different —R, —OR, —NRR or halogen groups, where each R is independently hydrogen, (C1-C6) alkyl or (C5-C14) aryl. The pentose sugar may be saturated or unsaturated. Exemplary pentose sugars and analogs thereof include, but are not limited to, ribose, 2'-deoxyribose, 2'-(C1-C6)alkoxyribose, 2'-(C5-C14)aryloxyribose, 2',3'-dideoxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose.

One or more of the pentose carbons of a nucleoside may be substituted with a phosphate ester having the formula:

where α is an integer from 0 to 4. In certain embodiments, α is 2 and the phosphate ester is attached to the 3'- or 5'-carbon of the pentose. In certain embodiments, the nucleosides are those in which the nucleotide base is a purine, a 7-deazapurine, a pyrimidine, a universal nucleotide base, a specific nucleotide base, or an analog thereof.

The term "nucleotide analog", as used herein, refers to embodiments in which the pentose sugar and/or the nucleotide base and/or one or more of the phosphate esters of a nucleoside may be replaced with its respective analog. In certain embodiments, exemplary pentose sugar analogs are those described above. In certain embodiments, the nucleotide analogs have a nucleotide base analog as described above. In certain embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counterions.

Also included within the definition of "nucleotide analog" are nucleotide analog monomers which can be polymerized into polynucleotide analogs in which the DNA/RNA phosphate ester and/or sugar phosphate ester backbone is replaced with a different type of linkage. Exemplary polynucleotide analogs include, but are not limited to, peptide nucleic acids, in which the sugar phosphate backbone of the polynucleotide is replaced by a peptide backbone.

The term "label" as used herein refers to any moiety that, when attached to a nucleotide or polynucleotide, renders such nucleotide or polynucleotide detectable using known detection methods.

The terms "complementary" or "complementarity" as used herein to refer to polynucleotides (i.e. a sequence of nucleotides or nucleotide analogs) related by Watson-Crick base-pairing rules. For example, for the sequence "A-G-T," is complementary to the sequence "T-C-A." Complementary may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

Samples

The target nucleic acids for use with the invention may be derived from any organism or other source, including but not limited to prokaryotes, eukaryotes, plants, animals, and viruses, as well as synthetic nucleic acids, for example. The target nucleic acids may originate from any of a wide variety of sample types, such as cell nuclei (e.g., genomic DNA), whole cells, tissue samples, phage, plasmids, mitochondria, and the like. The target nucleic acids may contain DNA, RNA, and/or variants or modifications thereof. The target may have been treated with bisulfite and other agents capable of inducing sequence differences capable of providing information regarding methylation patterns.

Many methods are available for the isolation and purification of target nucleic acids for use in the present invention. Preferably, the target nucleic acids are sufficiently free of proteins and any other interfering substances to allow adequate target-specific primer annealing and extension. Exemplary purification methods include (i) organic extraction followed by ethanol precipitation, e.g., using a phenol/chloroform organic reagent (Ausubel), preferably with an automated DNA extractor, e.g., a Model 341 DNA Extractor available from PE Applied Biosystems (Foster City, Calif.); (ii) solid phase adsorption methods (Walsh, 1991; Boom); and (iii) salt-induced DNA precipitation methods (Miller), such methods being typically referred to as "salting-out" methods. Optimally, each of the above purification methods is preceded by an enzyme digestion step to help eliminate protein from the sample, e.g., digestion with proteinase K, or other proteases. Other desirable methods of purification include use of NucPrep™ Chemistry from Applied Biosystems, through the ABI Prism™ 6100 Nucleic Acid PrepStation or the ABI Prism™ 6700 Automated Nucleic Acid Workstation.

To facilitate detection, the target nucleic acid can be amplified using a suitable amplification procedure prior to conducting the hybridization and ligation steps of the present invention. Such amplification may be linear or exponential. In a preferred embodiment, amplification of the target nucleic acid is accomplished using the polymerase chain reaction (PCR) (e.g., Mullis et al., 1994). Generally, the PCR consists of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon nucleic acid complementary to the target sequence, and (iii) a denaturation step which causes the separation of the amplicon from the target sequence. Each of the above steps may be conducted at a different temperature, preferably using an automated thermocycler (PE Applied Biosystems, Foster City, Calif.). In further embodiments, partial or whole genome amplification may be achieved by the use of strand displacement methods (Lizardi U.S. Pat. No. 6,124,120). In still further embodiments, partial or whole genome amplification may be achieved by the use of universal-tagged primers (Lao, et al., U.S. application Ser. No. 10/151061). A number of additional methods have been developed for exponential amplification of nucleic acids. These include the ligase chain reaction (LCR), self-sustained sequence replication (3SR), nucleic acid sequence based amplification (NASBA), strand displacement amplification (SDA), and amplification with Q.beta. replicase (Birkenmeyer and Mushahwar, J. Virological Methods, 35:117-126 (1991); Landegren, Trends Genetics 9:199-202 (1993)).

Samples may be derived from RNA, and can be converted to DNA/RNA heteroduplexes or to duplex cDNA by known methods (e.g., Ausubel; Sambrook). The method may then be employed to determine the relative difference between two samples from different sources. In some embodiments, RNA expression level between a plurality of RNA species between two samples from different sources is determined. In some embodiments, RNA is collected from tumor versus normal tissue. In some embodiments, RNA is collected from tissue of different developmental time points. In another embodiment, the relative amount of a particular SNP can be determined, for example between normal tissue and tumor tissue to determine loss of heterozygosity (for one non-limiting illustrative embodiment, see example below.). Samples may also be derived from microorganisms, benign or pathological.

Applications

A wide variety of infectious diseases can be detected by the process of the present invention. Typically, these are caused by bacterial, viral, parasite, and fungal infectious agents. The resistance of various infectious agents to drugs can also be determined using the present invention.

Bacterial infectious agents which can be detected by the present invention include *Escherichia coli, Salmonella, Shigella, Klebsiella, Pseudomonas, Listeria monocytogenes, Mycobacterium tuberculosis, Mycobacterium aviumintracellulare, Yersinia, Francisella, Pasteurella, Brucella, Clostridia, Bordetella pertussis, Bacteroides, Staphylococcus aureus, Streptococcus pneumonia*, B-Hemolytic strep., *Corynebacteria, Legionella, Mycoplasma, Ureaplasma, Chlamydia, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia*, and *Acitnomycetes*.

Fungal infectious agents that can be detected by the present invention include *Cryptococcus neoformans, Blastomyces dermatitidis, Histoplasma capsulatum, Coccidioides immitis, Paracoccidioides brasiliensis, Candida albicans, Aspergillus fumigautus, Phycomycetes (Rhizopus), Sporothrix schenckii, Chromomycosis*, and *Maduromycosis*.

Viral infectious agents that can be detected by the present invention include human immunodeficiency virus, human T-cell lymphocytotrophic virus, hepatitis viruses (e.g., Hepatitis B Virus and Hepatitis C Virus), Epstein-Barr Virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present invention include *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidum, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis,* trematodes, *Diphyllobothrium latum, Taenia* spp., *Pneumocystis carinii*, and *Necator americanis*.

The present invention is also useful for detection of drug resistance by infectious agents. For example, vancomycin-resistant Enterococcus faecium, methicillin-resistant *Staphylococcus aureus*, penicillin-resistant *Streptococcus pneumoniae*, multi-drug resistant *Mycobacterium tuberculosis*, and AZT-resistant human immunodeficiency virus can all be identified with the present invention.

Genetic diseases can also be detected by the process of the present invention. This detection can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

Cancers that can be detected by the process of the present invention generally involve oncogenes, tumor suppressor genes, or genes involved in DNA amplification, replication, recombination, or repair. Examples of these include: BRCA1 gene, p53 gene, APC gene, Her2/ Neu amplification, Bcr/Ab1, K-ras gene, and human papillomavirus Types 16 and 18. Various aspects of the present invention can be used to identify amplifications, large deletions as well as point mutations and small deletions/insertions of the above genes in the following common human cancers: leukemia, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

In the area of environmental monitoring, the present invention can be used for detection, identification, and monitoring of pathogenic and indigenous microorganisms in natural and engineered ecosystems and microcosms such as in municipal waste water purification systems and water reservoirs or in polluted areas undergoing bioremediation. It is also possible to detect plasmids containing genes that can metabolize xenobiotics, to monitor specific target microorganisms in population dynamic studies, or either to detect, identify, or monitor genetically modified microorganisms in the environment and in industrial plants.

The present invention can also be used in a variety of forensic areas, including for human identification for military personnel and criminal investigation, paternity testing and family relation analysis, HLA compatibility typing, and screening blood, sperm, or transplantation organs for contamination.

In the food and feed industry, the present invention has a wide variety of applications. For example, it can be used for identification and characterization of production organisms such as yeast for production of beer, wine, cheese, yogurt, bread, etc. Another area of use is with regard to quality control and certification of products and processes (e.g., livestock, pasteurization, and meat processing) for contaminants. Other uses include the characterization of plants, bulbs, and seeds for breeding purposes, identification of the presence of plant-specific pathogens, and detection and identification of veterinary infections.

Probe Composition

The primary probe set comprises one or more first primary probes and a second primary probe. The one or more first primary probes comprise a target specific portion, a target-identifying portion, and a primer portion. The target specific portions of the one or more first primary probes differ by one or more interrogator bases. In some embodiments the interrogator base is located at the 3' terminus of the one or more first probes of the primary probe set. In other embodiments, the interrogator base is not located at the terminus of the first and second probes of the primary probe set, but rather further within the target specific portion. In still other embodiments, the interrogator base is located at the 5' terminus of the one or more first probes of the primary probe set. Probes with target-specific portions that are fully complementary with their respective target regions can hybridize under stringent conditions. Probes with one or more mismatched bases in the target-specific portion, by contrast, will not hybridize to their respective target region. Both the one or more first probes along with the second probe of the primary probe set must be hybridized to the target for a ligation product to be generated. The second primary probe comprises a locus specific portion and a primer portion. By convention, the one or more first probes of the primary probe set may be considered upstream (i.e. 5' to) the second primary probe. The secondary probe set comprises one or more first secondary probes, and a second secondary probe. The one or more first secondary probes comprise a primer portion. The second secondary probe comprises a target-identifying portion. By convention, the one or more first probes of the secondary probe set may be considered upstream (i.e. 5' to) the second secondary probe. It will be appreciated that this designation is arbitrary, and the one or more first probes of the primary probe set, the one or more first probes of the secondary probe set, or both, may be downstream (i.e. 3' to) the second primary or secondary probes without straying from the scope of the invention. It will further be appreciated that in many situations, designation of the two strands of a duplex target as a "target strand" and "complement of the target strand" will be an arbitrary choice, so that reversal of these designations may also be appropriate. For example, a gene-coding strand can be designated as a "target strand" or as a "complement of a target strand", depending on the preference of the user. Alternatively, both strands of a target duplex can be referred to as "target strands". Further, target may refer to both the original sample, as well as the first ligation product as well as the optional amplification product. Also, when multiple probe pairs are used to detect a multiple possible target sequences in a sample, it will be appreciated that the different target sequences may be present in the same target strand (i.e., in the sample chromosome or same restriction fragment) or may be present in different strands. For this reason, the phrase "target polynucleotide strand region" or "target strand region" is used to refer to a target sequence regardless of whether two different target sequences are present in the same strand. It will also be appreciated that the invention further contemplates a second set of primary or secondary probes complementary to the complement of the single-stranded target, thereby allowing for exponential amplification in an LCR-type reaction, see Bi et al., U.S. Pat. No. 6,511,810, which is incorporated herein by reference in its entirety.

In some embodiments, the one or more first probes of the primary probe set further comprise one or more marker nucleotides between the primer-specific portion and the target-specific portion. The sequence of the marker nucleotides encodes the identity of the interrogator base. For example, in a SNP detection embodiment, the sequence of the marker nucleotides can encode the identity of the allele present at a particular SNP locus. The one or more first probes of the secondary probe set of the second ligation reaction can utilize these marker nucleotides to determine the identity of the target.

Probe Chemistry

The present invention employs primary probe pairs designed to hybridize to a complementary target sequence, and which may be capable of ligation when hybridized to the target sequence. The present invention also employs secondary probe pairs designed to hybridize to their complementary sequence on the first ligation product, and which may be capable of ligation when hybridized to the first ligation product. The primary or secondary probe pairs are useful, for example, in linear and exponential probe ligation methods described herein and incorporated by reference herein, which result in the identification of one or a plurality of target sequences. Any of a variety of different probe constructs and configurations can be used, as will be more fully understood from the following discussion.

In some embodiments, probes are comprised of DNA. In other embodiments, probes may be comprised of LNA (Mouritzen et al., 2003). In other embodiments, probes may be comprised of PNA, as described in (Chen et al., U.S. Pat. No. 6,469,151). In other embodiments, probes may be comprised of L-ZDNA. In yet further embodiments, probes may be comprised of other nucleic acid analogs and bases, for example intercalating nucleic acids (INAs, as described in Christensen and Pedersen, 2002), and AEGIS bases (Eragen, U.S. Pat. No. 5,432,272). It will be appreciated that the introduction of varying amounts of nucleic acid analogs can be exploited to alter the melting temperature of the probes in such ways as necessary to optimize the hybridization reaction conditions. Probes can be prepared by any suitable method, preferably using an automated DNA synthesizer and standard chemistries, for example phosphoramidite chemistry (Beaucage; Gait, 1984, 1990). It will further be appreciated that probes may be synthesized to include a 5' phosphate group exploited by ligase biochemistry. Said 5' phosphate group may also be introduced through a kinase reaction, for example through the use of T4 polynucleotide kinase.

In some embodiments, probes may further comprise a mobility modifying moiety thereby imparting a recognizable identifying mass. Non-limiting examples of mobility modifying moieties are described in Grossman et al., U.S. Pat. No. 5,514,543, and Woo et al., U.S. application Ser. No. 09/836704, which are incorporated herein by reference. Further, mobility modification may be achieved by introducing a known number of nucleotides (e.g. a specified number of thymidine residues) to a given probe.

In some embodiments, the one or more first probes of the primary probe set may be individually joined to the second probe, thereby forming a near-circle when hybridized to the target. By varying the interrogator base between the target specific portions of the first probe and the second probe, hybridizaton of the correct joined probe to target results in a ligateable nick, thus forming an amplifiable circle.

In some embodiments, one of the probes may comprise a label. The skilled artisan will appreciate that many labels may be used in various embodiments of the present invention. For example, labels include, but are not limited to, fluorophores, radioisotopes, chromogens, enzymes, antigens, immunologically detectable haptens, heavy metals, dyes, magnetic probes, spin labels, phosphorescence groups, chemiluminescent groups, energy-transfer fluorescent dyes, electrochemical detection moieties, Quantum Dots (Xu et al., 2003), and intercalating nucleic acids (Christensen and Pedersen, 2002). Labels are well known to those skilled in the art and numerous examples can be found in the Handbook of Fluorescent Probes and Research Chemicals 6th Edition, Richard Haugland, Molecular Probes, Inc., 1996 (ISBN 0-9652240-0-7). Labels also include, but are not limited to, elements of multi-element indirect reporter systems, e.g., biotin/avidin, antibody/antigen, ligand/receptor, enzyme/substrate, and the like, in which the element interacts with other elements of the system in order to effect a detectable signal. One exemplary multi-element reporter system includes a biotin reporter group attached to a primer and an avidin conjugated with a fluorescent label. Detailed protocols for methods of attaching reporter groups to oligonucleotides and polynucleotides can be found in, among other places, G. T. Hermanson, *Bioconjugate Techniques*, Academic Press, San Diego, Calif. (1996) and S. L. Beaucage et al., *Current Protocols in Nucleic Acid Chemistry*, John Wiley & Sons, New York, N.Y. (2000). Examples of nonlimiting suitable labels are described in U.S. Pat. No. 5,770,716. Additional reviews of methodologies for labeling DNA provide guidance applicable to the present invention, and include Matthews et al. (1988); Haugland (1992), Keller and Manak (1993); Eckstein (1991); Kricka (1992). Additional moieties for creating labeled nucleotides are described in Fung et al.; Hobbs et al., Menchen et al., and Bergot et al., and Rosenblum et al. (all supra). In yet another embodiment, ligation is detected or quantified using an intercalating dye such as ethidium bromide or SYBR GREEN (Molecular Probes) or a minor groove binder such as Hoechst 33258, for example, which are compounds that exhibit increased fluorescence in proportion to the amount of double-stranded nucleic acid in a sample Probing Function In some embodiments, probes may be hybridized directly adjacent to one another in a ligation-competent fashion. However, in other embodiments, hybridized probes may be treated to generate a ligation-competent complex. For example, in some embodiments, a ligation-competent complex may be achieved by using overlapping probes, such that the 5' end of the downstream probe is cleaved in a flap endonuclease-type procedure (Bi et al., U.S. Pat. No. 6,511, 810). In other embodiments, gap-filling and single nucleotide extension type procedures may be employed to generate a ligation-competent complex (see U.S. Pat. No. 5,185, 243, European Patent Applications EP 32038 and EP 439182, and published PCT Patent Application WO 90/01069, which are all incorporated by reference herein). In other embodiments, the phosphorylysis may be employed to remove 3' nucleotides, thereby generating a ligation competent complex, see Liu and Sommer, 2002).

Ligation Overview

Ligation-competent probe complexes are ligated together using a variety of procedures, including enzymatic and chemical methods. Numerous ligase enzymes are known in the art and can be obtained from a variety of biological and commercial sources. Exemplary ligases include, but are not limited to, *E. coli* ligase, T4 ligase, T. aquaticus ligase, T. Thermophilus ligase, Pfii ligase, etc. (see, for example, U.S. Pat. No. 5,830,711 (Barany et al.) and EP Patent 320308 B1 (Backman and Wang). A thermostable ligase is preferred so that there is no need to replenish ligase activity during temperature cycling. In an exemplary embodiment, the thermostable ligase retains at least 80% of initial 5' nuclease activity after thirty cycles of 65° C. for 1 min. (annealing/extension) and 95° C. for 15 seconds (strand denaturation). In another embodiment, ligation is performed using the ligase AK16D (described in Published U.S. application 9925437).

Although it is preferred that ligation is carried out using a ligase enzyme, chemical (non-enzymic) ligation is also contemplated. In one embodiment, chemical ligation can be performed by generating a chemically reactive group at the 5' end of the remaining fragment of the second probe that is capable of reacting with a corresponding reactive group at the 3' end of hybridized first probe. When the 3' base of the first probe is immediately contiguous with the 5' base of the fragment of the second probe, and the 3' base and 5' base are hybridized to matching bases in the target strand region, the two reactive groups form a covalent linkage due to mutual close proximity. The reaction occurs at the temperature of the reaction mixture and does not require illumination with high-energy light, although microwave irradiation can be used to facilitate ligation. For example, the first probe can be designed to contain a 3, bromoacetyl amino group, and the second probe can be designed to contain a phosphorothio ate linkage at the site that is to be cleaved. Cleavage of the second probe produces a 5' thiophosphate group that is immediately contiguous with the 3' bromoacetyl amino group. Displacement of the bromine by the sulfur atom of the thiophosphate group produces a thiophosphorylacylamino. linkage between the first probe and the remaining second fragment of the second probe. The resultant ligated strand can then be detected or can serve as a template for hybridization, cleavage, and ligation of a complementary second probe pair, as appropriate with various embodiments of the invention. Guidance for exemplary chemical groups that may be used for thermal chemical ligation can be found, for example, in U.S. Pat. No. 5,476,930 (Letsinger and Gryaznov), U.S. Pat. No. 5,741,643 (Gryaznov et al.), and references cited therein. Chemical ligation by photoexcitation is also contemplated, as described in EP Patent 324616 B1 (Royer et al.), for example. The invention further contemplates nonenzymatic autoligation as discussed in Kool et al., Nature Biotechnology, Volume 19, 148-152.

First Ligation

The primary probe set comprises one or more first primary probes and a second primary probe. The one or more first primary probes comprises a target specific portion, a target identifying portion, and a primer portion. The second primary probe comprises a target-identifying portion and a primer portion. By convention as used herein, the one or more first probes of the primary probe set may be considered upstream (i.e. 5' to) the second primary probe. Some embodiments of the invention contemplates a second set of primary probes that may be complementary to the complement of the single-stranded target, thereby allowing for exponential amplification in an LCR-type reaction (for example, Barany et al., U.S. Pat. No. 5,494,810). It will further be appreciated that any of the techniques discussed below under the Amplification section may be employed to amplify the first ligation product.

Removal of Unligated Probes

It will be appreciated that removing unreacted probes from the ligation reaction prior to subsequent reactions may be desirable in order to remove potentially competing molecules, for example to minimize primer dimer formation in an optional amplification reaction. Certain embodiments of the invention may employ one or more of the many procedures that exist for removing unreacted probe species. Examples of such removal procedures are provided below.

Removal of Unligated Probes by Dilution

In one embodiment, the contribution of unreacted probe species of the first ligation reaction may be reduced by diluting the reaction mixture prior to amplification. In some embodiments the first ligation reaction mixture is diluted at least about 200 fold. In some embodiments the first ligation reaction mixture is diluted at least about 100 fold. In some embodiments the first ligation reaction mixture is diluted at least about 50 fold. In some embodiments the first ligation reaction mixture is diluted at least about 10 fold. In some embodiments the first ligation reaction mixture is diluted at least about 5 fold. In some embodiments the first ligation reaction mixture is diluted at least about 2 fold.

Removal of Unligated Probes by Nucleases

A variety of nucleolytic enzymes exist with varying specificities that can be used for the purposes of removing unreacted (i.e. unligated) probe species from the ligation reaction. In certain embodiments the unreacted probes may serve as substrate for the nuclease, whereas the ligation products are not substrates. For example, lamba exonuclease degrades nucleic acids bearing a free 5' phosphate group. By capping the upstream probes with a 5'OH blocking group, unreacted downstream probes bearing a 5'P can be degraded while leaving the correct ligation product in tact. Other exemplary 3' blocking groups include 3' deoxy, 3' phosphate, 3' N-acetyl, 3' O-trityl, 3' O-monomethoxytrityl, etc. In yet another example of nuclease removal of unreacted probes, Exonuclease III degrades nucleic acids bearing a free 3' hydroxyl group. By blocking the 3' hydroxyl group of only the downstream probes, unligated upstream probes bearing the 3-hydroxy group may be degraded. In other embodiments, uracil N-glycosylase may be employed to remove unreacted probes, wherein the probes contain uracil residues in place of thymine residues. Conversion of the ligation product, and hence its uracil residues into adenine residues, results in the selective resistance of the synthesized ligation product to the nuclease activity of uracil-N-glycosylase.

Kits for performing these types of reactions are commercially available (e.g. the AmpErase® kit from Applied Biosystems). The invention contemplates heat-labile versions of uracil-N-gyclosyslase, described for example by Roche. The invention further contemplates a combination of these nuclease-based approaches. Further elaboration on such nuclease-mediated digestion schemes can be found in U.S. Pat. No. 6,027,889, incorporated herein by reference.

Removal of Unligated Probes by Affinity-Moiety Interactions

Affinity-moiety interactions are used in a variety of molecular biology procedures for purifying and separating heterogeneous reaction mixtures. Exemplary affinity-moiety pairs include without limitation, ligands and their receptors, including but not limited to, avidin-biotin, streptavidin-biotin, and derivatives of biotin, streptavidin and/or avidin, including but not limited to desthiobiotin, NeutrAvidin, CaptAvidin, and the like; binding proteins/peptides, including but not limited to maltose-maltose binding protein (MBP); calcium-calcium binding protein/peptide (CBP); antigen-antibody, including but not limited to epitope tags, including but not limited to c-MYC (e.g., EQKLISEEDL), HA (e.g., YPYDVPDYA), VSV-G (e.g., YTDIEMNRLGK), HSV (QPELAPEDPED), V5 (e.g., GKPIPNPLLGLDST), and FLAG Tag™ (e.g., DYKDDDDKG), and their corresponding capture moieties including but not limited to anti-epitope antibodies or immunoreactive portions of the corresponding anti-epitope antibody; haptens, for example but not limited to dinitrophenyl and digoxigenin, and their corresponding antibody molecules or immunoreactive portions of antibody molecules; aptamers and their corresponding targets; zip code sequences and their complements; poly-His tags and their substrates, such as immobilized metal ion affinity chromatography (IMAC) materials and also antibodies or immunoreactive portions of anti-poly-His tags; and the like. In some embodiments, by incorporation of an affinity binding partner into one of the probes, affinity-moiety binding interactions may be employed to remove unligated probes. In some embodiments, biotin may be added to the downstream probe, thereby allowing streptavidin-based separation of downstream probes and ligation products from unligated upstream probes. Unligated upstream probes can then be removed. The converse may also be employed, in which upstream probes are biotinylated, and unligated downstream probes subsequently removed. The invention further contemplates a combination of nuclease-mediated digestion with affinity-moiety based pull out. In some embodiments, upstream probes are biotinylated, while downstream probes comprise a polymer block at their 3' end, thereby allowing exonuclease-mediated degradation of unligated upstream probes with their exposed 3' end, and purification of the ligation product with streptavidin away from the unligated non-biotinylated downstream probes.

Decontamination

In some embodiments, uracil may be included in the amplification reaction, thereby generating amplification products with uracil substituted for thymine. Uracil-N-glycosylase may then be employed by well-known techniques to decontaminate subsequent reactions (see Gelfand et al., U.S. Pat. No. 5,418,149, and Applied Biosystems GeneAmp® PCR Carryover kit). The invention contemplates heat-labile versions of uracil-N-gyclosyslase, described for example by Roche, to facilitate removal of uracil-N-gyclosyslase following its desired activity.

Amplification

In one embodiment, exponential amplification of the ligation product is achieved by a polymerase chain reaction, exploiting the primer portions of the ligation product. In another embodiment, linear amplification of the ligation product may be achieved by cycling the hybridization-ligation steps in an oligonucleotide ligation type assay (OLA) by ligase detection reaction (LDR) (Barany et al., U.S. Pat. No. 6,027,889). In another embodiment, exponential amplification of the ligation product may be achieved by a Ligase Chain Reaction-type procedure (LCR) (Barany et al., U.S. Pat. No. 5,494,810). In another embodiment, exponential amplification of the ligation product is achieved by Flap-endonuclease and LCR (Bi et al., U.S. Pat. No. 6,511,810). A number of other methods have been developed for exponential amplification of nucleic acids and may be employed to amplify the sample in the current method. These include self-sustained sequence replication (3SR), nucleic acid sequence based amplification (NASBA), strand displacement amplification (SDA), and amplification with Q.beta. replicase (Birkenmeyer and Mushahwar, J. Virological Methods, 35:117-126 (1991); Landegren, Trends Genetics 9:199-202 (1993)).

Second Ligation

The secondary probe set comprises one or more first secondary probes and a second secondary probe. The one or more first secondary probes comprise a primer portion. The second secondary probe comprises a target-identifying portion. By convention, the one or more first probes of the secondary probe set may be considered upstream (i.e. 5' to) the second secondary probe. In some embodiments of the invention a second set of secondary probes may be complementary to the complement of the single-stranded target, thereby allowing for exponential amplification in an LCR-type reaction (for example, Barany et al., U.S. Pat. No. 5,494,810). It will further be appreciated that any of the techniques discussed above under the Amplification section may be employed to amplify the second ligation product.

In some embodiments, the one or more first secondary probes are complementary to the primer portion of the first ligation product, while the second secondary probe is complementary to the target-identifying portion of the first ligation product. In those embodiments wherein the identity of a SNP is to be detected, the primer-specific portion of the one or more first probes of the primary probe set may encode the identity of the allelic variants, while the target-specific portion of the second probe of the primary probe set may encode the identity of the SNP locus. Following the first ligation and optional amplification, the one or more first probes of the secondary probe set may encode the identity of the allelic variant, while the second probe of the secondary probe set may encode the identity of the genomic locus of the single nucleotide polymorphism. In some embodiments, the one or more first probes of the secondary probe set are differentially labeled, while the second probe of the secondary probe set comprises a mobility-modifying moiety. Following the second ligation, products can be separated and the identity of the target sequence ascertained by the label and mobility of the product of the second ligation reaction.

In some embodiments of the invention, a universal set of target identifying portions are used in conjunction with two universal primers, thereby increasing multiplexy while minimizing reagent complexity. In a nonlimiting illustrative embodiment, the identity of a plurality of SNPs in a first pool are to be determined in a first well of a microtitre plate, and the identity of a plurality of SNPs in a second pool are to be determined in a second well. The SNP loci of the first pool differ from the SNP loci of the second pool. In such an embodiment, the same target identifying portion may be used to identity both the first SNP locus of the first pool in the first well, and the different SNP locus of the second pool in the second well. Because the same target identifying portion is paired with a different target specific portion in the first pool as compared to the second pool, the redundant and economic use of target identifying portions across different SNP loci may be accomplished. Further, through their pairing with different interrogator bases in the first well at the first SNP locus, the universal primer portions of the first and second primary probes may encode allelic identity of the first SNP locus. Through their pairing with different interrogator bases in the second well, the same universal primer portions of the first probes of the primary probe set may encode allelic identity of the second SNP locus. Following the first ligation and optional amplification, the second ligation can exploit universal target identifying portions and primer portions introduced in the first ligation reaction with a complementary primer portion comprising a label, and a complementary target-identifying portion comprising a mobility modifying moiety. As a result, a finite number of primer-portion, target-identifying probes in the second ligation reaction may be used to determine the identity of an infinite number of allelic variants. This method maximizes specificity by requiring two successful ligation events to produce the detected product. Further, this method minimizes variable probe content by using a finite pool of target-identifying portions and finite pool of universal primer portions, thereby reducing the cost and complexity of identifying a plurality of SNPs.

Separation

The target sequence or sequences can be detected or quantified in any appropriate way. Target detection or quantification can be based on the presence of any species or complex that either is not present in the reaction mixture unless the target is present, or is present in an amount greater than the amount of that species that would otherwise be present in the absence of the target sequence.

Mobility dependent analysis techniques (MDAT) may be employed for separation, and comprises an analytical technique based on differential rates of migration between different analyte species. Exemplary mobility-dependent analysis techniques include electrophoresis, chromatography, mass spectroscopy (including MALDI-TOF instruments, HPLC, gel filtration, sedimentation, e.g., gradient centrifugation, field-flow fractionation, multi-stage extraction techniques, and the like. Each species can be detected based on a unique property, such as electrophoretic mobility, mass, or a particular detectable label (or detectable signal associated with such label). Methods for electrophoretic separation of nucleic acids and other species are well known, and are described, for example in the works of Ausubel (1993, and later editions) and Sambrook et al. (2001). The invention also contemplates the use of probes that have distinct electrophoretic mobilities due to the presence of polymer segments or other moieties that confer distinct mobilities to the detected species in sieving or non-sieving media, as taught in U.S. Pat. Nos. 5,470,705, 5,514,543, and 5,580,732 (Grossman et al.), and Woo et al., U.S. application Ser. No. 09/836704, for example. In some preferable embodiments, separation is achieved by the use of an Applied Biosystems sequencer, for example models 3700, 3730, and 3730x1.

Multiple Targets; Arrays

The present invention can be used to detect a plurality of different target sequences in a single sample or in a plurality of samples. In one embodiment, different target sequences are detected separately in separate reaction mixtures. In another embodiment, a sample can be contacted with a plurality of primary probe sets that are each designed to detect a different target sequence that may be present in the sample. The various target sequences can be detected based on detectable characteristics that are unique for each secondary probe pair, such as mass, electrophoretic mobility, fluorescence signal, or a combination thereof. Methods of electrophoresis are well known and are described, for example, in Ausubel, Sambrook et al. (1989), and Grossman and Colburn (1992). The number of target sequences, and corresponding probe pairs, that can be used in a single reaction mixture is a matter of choice by the user, and will depend in part on the resolvability of the properties that are used to distinguish the various reaction products.

Target identifying portion containing fragments of the second ligation reaction can be separated from each other by hybridization to corresponding target identifying portions that are immobilized on distinct solid support regions. Preferably, the solid support regions are configured as an addressable array. By "addressable array" is meant that the identity of each probe or probe fragment is known or can be determined from the position of hybridization of that probe or probe fragment on the array. Preferably, the target identifying portions are immobilized in discrete regions on a planar surface, such that each discrete region contains only target identifying portions having a particular sequence, and such that the sequence of the target identifying portion at each different discrete region is known. Conveniently, the target identifying portions may be distributed as a periodic two-dimensional array of discrete target identifying portion regions which can be indexed via X and Y coordinates, or any equivalent thereof.

Solid phase supports can be formed using any material that allows for the target identifying portion segments to hybridize specifically to their complementary target identifying portions on the support. Exemplary support materials include glass; quartz; silicon; polycarbonate; metallic materials such as GaAs, copper, or germanium; a polymerized gel, such as crosslinked polyacrylamide; or membranes such as nylon, polyvinylidine difluoride (PVDF), or poly-tetrafluoroethylene.

Immobilization of target identifying portions in the array may be accomplished using any of a variety of suitable methods. In one approach, the target identifying portion complements are deposited onto a solid phase surface using liquid dispensing methods. For example, deposition can be accomplished robotically on a poly-lysine-coated microscope slide, followed by treatment with succinic anhydride to couple the tag complements to the polylysine moieties, as described by Schena et al. (1995) and Shalon (1995). For covalent attachment, the tag-complements may include a suitably reactive functionality for covalent attachment to the support. Exemplary linking chemistries are disclosed in Barany et al. (1991), Pon et al. (1988), and Menchen et al. (1994).

In another approach, target identifying portion complements can be synthesized on a support by photolithographic methods, as described in Fodor et al. (1991, 1995), Pirrung et al. (supra), and Shoemaker (1997). Photoremovable groups are attached to a substrate surface, and light-impermeable masks are used to control the addition of monomers to selected regions of the substrate surface by activating light-exposed regions. Monomer addition to the growing polymer chains is continued using different mask arrangements until the desired, different sequence target identifying portion complements are formed at the desired addressable locations. The masking method of Fodor et al. may also be modified to accommodate block-polymer synthesis. For example, an array of linker groups (e.g., a polypeptide, or an N-protected aminocaproic acid linked to an aminopropyl group) can be formed on the substrate surface via simultaneous activation of all immobilization regions to form a "carpet" of linker groups. The target identifying portion complements are then individually deposited on (or adsorbed to) the substrate surface as liquid drops at selected addressable locations, and are exposed to light or heat as appropriate to couple the binding moieties to the immobilized linker groups, preferably while a sufficient amount of solvent still remains from each drop.

Alternatively, the target identifying portion complements may be immobilized on the support(s) non-covalently, e.g., using ligand-receptor type interactions. For example, the target identifying portion complements may contain covalently attached biotin groups as linker groups, for binding to avidin or streptavidin polypeptides which have been attached to a support (e.g., Barrett, 1996).

Linker segments may also be included between the target identifying portion complement sequence and the support to provide a spacer arm which allows the target identifying portion specific binding region to separate from the support, rendering the binding region more accessible to the sample. Exemplary linker groups are described, for example, in Fodor et al. (1995) and Brenner (PCT Publications cited above). Preferably, the tag complement is separated from the support by a chain comprising at least 10 chain atoms.

The support may include depressions in the support for holding the deposited target identifying portion complements. Elevated protrusions can also be used, onto which the target identifying portion complements are deposited. In yet another approach, target identifying portion complements can be formed on beads as described in U.S. Pat. No. 5,846,719 (Brenner et al.), for example. Alternatively, target identifying portion complements are attached to an array of individual beads attached to a surface, via magnetic force if the beads are magnetic (Albretsen, 1990), or with an adhesive.

In another approach, the ligation reaction can be performed directly on an array, wherein for example one of the probes is immobilized, and the target and the other probe form a complex that can be ligated.

In another approach, an array is formed on a substrate, such as a glass plate, that is covered with a rectangular array of pieces of polyacrylamide gel (e.g., Khrapko et al., 1991). A different target identifying portion complement is deposited at a selected site and is bound thereto by reacting a 3'-terminal dialdehyde on the target identifying portion complements with hydrazide groups on the polyacrylamide gel piece. Target identifying portion complement arrays in accordance with the invention may also be formed by robotic deposition of target identifying portion complements onto nylon (Khrapko et al., supra). Following deposition, immobilization of the target identifying portion complements may be facilitated by heat or photoactivation as appropriate.

To reduce the amounts of assay reagents used for target identifying portion detection, arrays may be formed as microarrays having target identifying portion complement region densities of greater than 100 regions/cm$^2$, 300 regions/cm$^2$, $10^3$ regions/cm$^2$, $3 \times 10^3$ regions/cm$^2$, $10^4$ regions/cm$^2$, 10$^5$ regions/cm$^2$, or 10$^6$ regions/cm$^2$. In addition, the number of different sequence target identifying portion complements in each array is preferably equal to or greater than 10, 20, 50, 100, 200, 500, 1000, 3000, 10,000, 30,000, 100,000, or 300,000.

The target identifying portion and target identifying portion complements may be single or double stranded, such that sequence specific hybridization forms either duplexes by Watson and Crick base-pairing, or triplexes by forward or reverse Hoogsteen bonding. In embodiments where specific hybridization occurs via triplex formation, coding of target identifying portion sequences follows the same principles as for duplex-forming target identifying portions. However, there are further constraints on the selection of word sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. Furthermore, the invention also contemplates the use of non-standard base pairing moieties such as disclosed in U.S. Pat. No. 5,432,272 (Benner) and which are available from Eragen as the "AEGIS" system, as well as intercalating nucleic acids (Christensen and Pedersen, 2002).

There is extensive guidance in the literature for selecting appropriate sequences, orientation, conditions, nucleoside type (e.g. whether ribose or deoxyribose nucleosides are employed), base modifications (e.g. methylated cytosine, and the like in order to maximize, or otherwise regulate, triplex stability as desired in particular embodiments, e.g., Brenner (supra). More generally, conditions for annealing single-stranded or duplex tags to single-stranded or duplex sequence complements are well known, e.g. Brenner (supra), Ji et al. (1993), Cantor et al. (supra), Wetmur (1991), Breslauer et al. (1986), Schena (1995), and the like.

Detection and Quantification

Any detection method may be used which is suitable for the type of label employed. Thus, exemplary detection methods include radioactive detection, optical absorbance detection, e.g., UV-visible absorbance detection, optical emission detection, e.g., fluorescence or chemiluminescence.

In some embodiments, captured tagged species can be detected on an array by scanning all or portions of each array simultaneously or serially, depending on the scanning method used. For fluorescence labeling, selected regions on an array may be serially scanned one-by-one or row-by-row using a fluorescence microscope apparatus, such as described in Fodor (1995) and Mathies et al. (1992). Hybridization patterns may also be scanned using a CCD camera (e.g., Model TE/CCD512SF, Princeton Instruments, Trenton, N.J.) with suitable optics (Ploem, 1993), such as described in Yershov et al. (1996), or may be imaged by TV monitoring (Khrapko, 1991). For radioactive signals (e.g., $^{32}$P), a phosphorimager device can be used (Johnston et al., 1990; Drmanac et al., 1992; 1993). Other commercial suppliers of imaging instruments include General Scanning Inc., (Watertown, Mass., www.genscan.com), Genix Technologies (Waterloo, Ontario, Canada; www.confocal.com), and Applied Precision Inc. Such detection methods are particularly useful to achieve simultaneous scanning of multiple tag complement regions.

In some embodiments, detection and quantitation may also be achieved using fluorescence labels on a capillary electrophoresis, for example the Applied Biosystems 3730x1.

Measured signals can be analyzed manually or by appropriate computer methods to tabulate results. The results can be measured to provide qualitative or quantitative results, depending on the needs of the user. Reaction conditions may include appropriate controls for verifying the integrity of hybridization, calibrating migration rates of mobility modified products, and for providing standard curves for quantitation.

Kits

The invention also contemplates kits that are useful in practicing the invention. Such kits may include one or more primary and secondary probe sets as discussed above, and optionally, a ligase enzyme and other enzymes required for polymerization, digestion of unligated probes, and decontamination of subsequent reactions. The kit may also include buffers and any other reagents that facilitate the method.

From the foregoing, it can be seen how the features and benefits of the invention can be achieved. The invention provides a convenient method for determining the presence or absence of one or more target sequences, and for quantification as well. The method is amenable to high-throughput processing of many target sequences and many different samples. The invention can be used for a variety of purposes, such as genetic screening, allele determination, sample identification, disease diagnosis, forensics, agricultural analysis, and many others. The method can also be used to establish a sequence profile of one or more samples, for identifying or distinguishing samples. The invention will be better appreciated and understood in the context of the following non-limiting schematics and examples.

EXAMPLE

Figure 1:
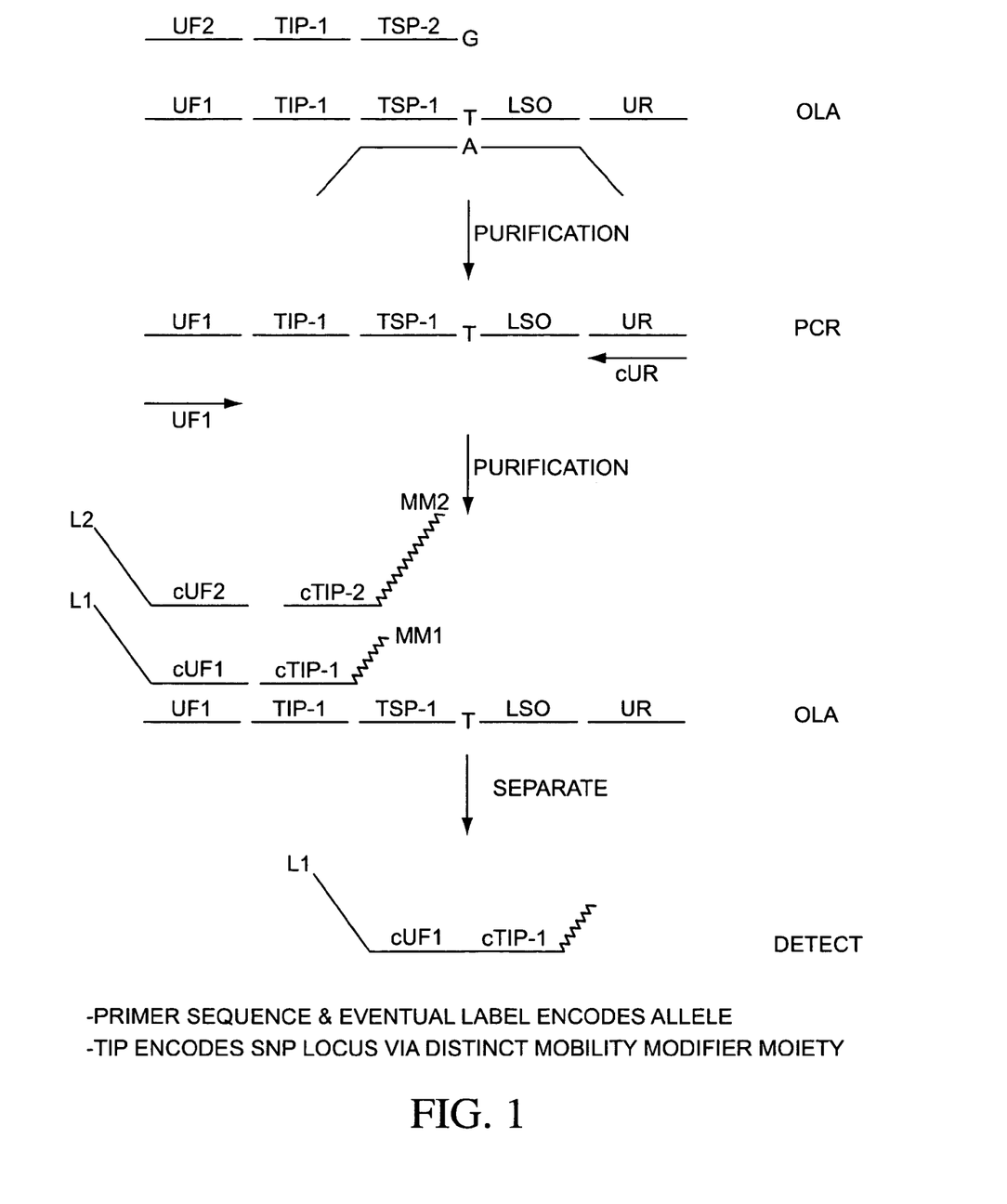
FIG. 1 illustrates a general schematic illustrative of the inventive method.
Figure 2:
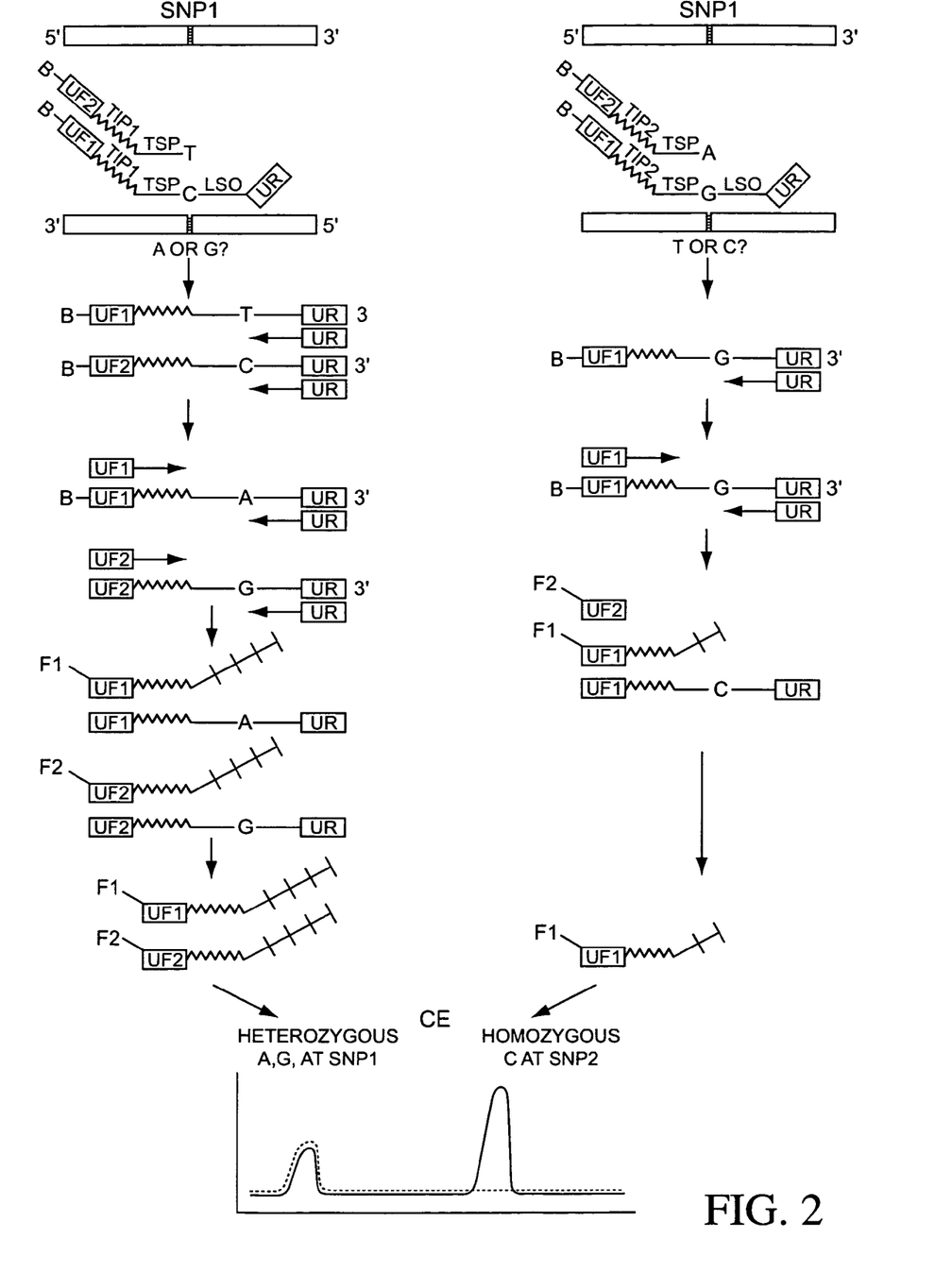
FIG. 2 illustrates one embodiment of the invention in which the identity and genotype of a SNP of interest is interrogated using the OLA-PCR-OLA method comprising biotin-affinity moiety purification with capillary electrophoresis detection. For ease of display, only two SNP loci are shown, but it will be appreciated that the invention further comprises identifying a plurality of target SNP loci.
Figure 3:
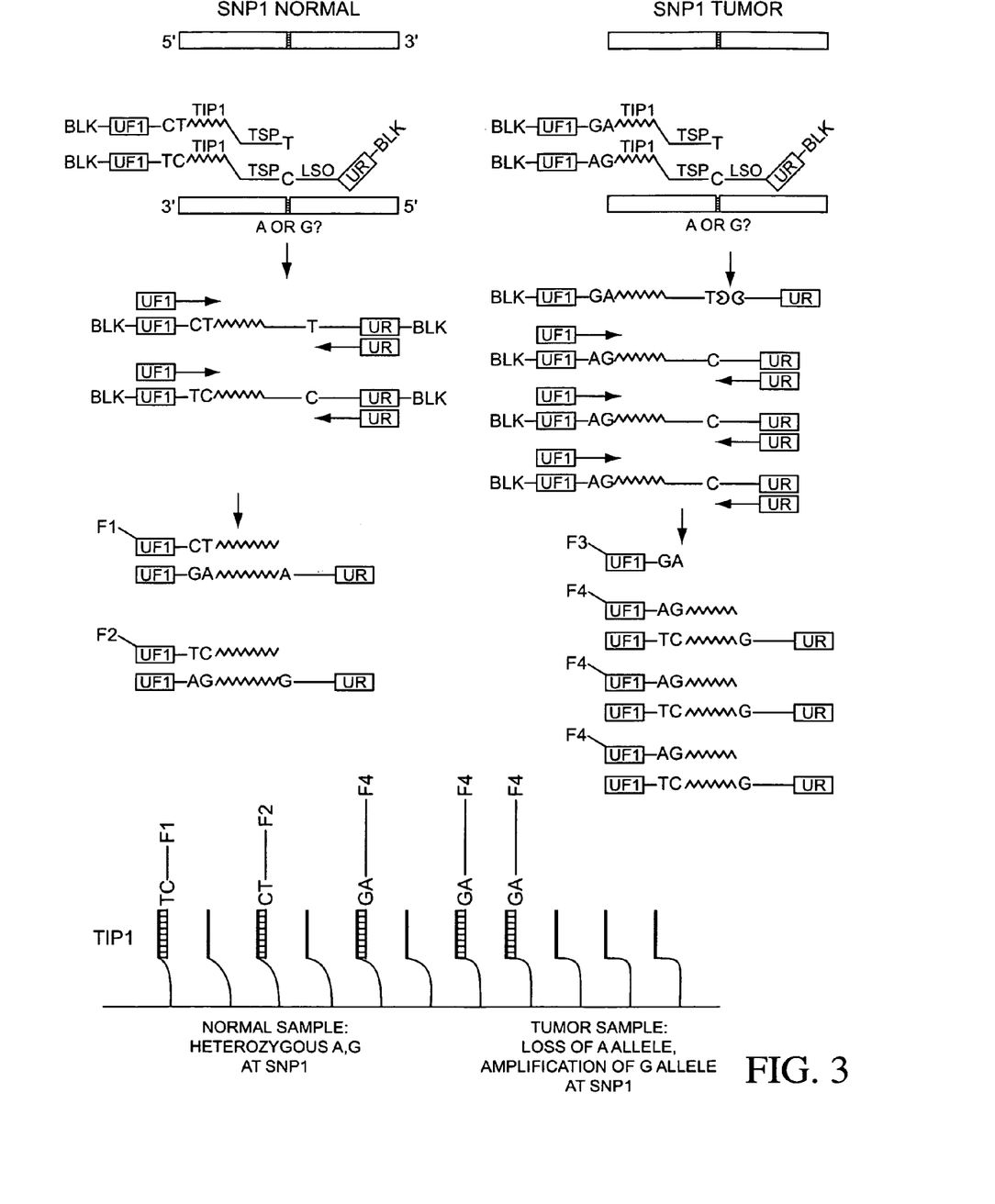
FIG. 3 illustrates one embodiment of the invention in which the identity and relative proportion of a SNP is compared between a normal sample and a tumor sample using the OLA-PCR-OLA method comprising enzymatic purification with array detection. For ease of display, only one SNP locus is shown, but it will be appreciated that the invention further comprises identifying a plurality of target SNP loci.

Genomic DNA preparation: Genomic DNA is obtained from the Coriell Institute for Medical Research (Camden, N.J.) and prepared by conventional preparation methods.

Probe Synthesis:

Probes are synthesized by standard phosphoramite methods with phosphorylation of the 5' end as required.

First LDR Reaction:

Reaction components for the first LDR comprise 1 ul 10× ligase buffer (comprising 7 mM MgCl2, 20 mM MOPS pH 7.5, 0.1% Triton X100, 1 mM DTT, 0.25 mM NAD) 1 ul of 100 nM first primary probe 12 plex mix, 1 ul of 100 nM first primary probe 12 plex mix, 1 ul 100 nM second primary probe 12 plex mix, 0.25 ul (40 units/ul) Ligase, 4.75 ul ddH20, comprising a reaction volume of 9 ul. The reaction is cycled 100 times with a 95 C. melting step for 10 s, 60 C. annealing/ligation step for 30 s. After the 100 cycles, reaction is held at 4 C.

Post Ligation Purification:

Reaction components for the post-ligation purification comprise 0.5 ul 10× buffer (comprising 67 mM Glycine-KOH pH9.4, 2.5 mM MgCl2, 50 ug/ml BSA), 1 ul Exonuclease 1 (20 units/ul), 0.4 ul Lamba exonuclease (5 units/ul), 7.5 ul ddH20, thereby forming a reaction volume of 9 ul to which is added 1 ul of the first LDR product. The enzymatic digestion reaction then proceeds at 37 C. for 30 minutes, following by a degradation step for the enzymes themselves of 95 C. for 20 minutes. The reaction is then held at 4 C.

Amplification:

Reaction components for the amplification reaction comprise 5 ul Amplitaq Gold (2× stock), 1 ul Uni1PCR37 primer (10 uM stock), 1 ul Uni2PCR38 primer (10 uM stock), and 2 ul ddH2O, totaling a reaction of volume of 9 ul to which is added 1 ul of the enzymatically digested product. The amplification reaction is achieved by a PCR, the steps of which comprise an initial 95 C. melt, followed by 35 cycles of 95 C. for 10 s and 60 C. for 1 minute. After the 35 cycles, the reaction is held at 4 C.

Second Ligation:

Reaction components for the second ligation reaction comprise 1 ul 10× ligase buffer (comprised of 7 mM MgCl2, 20 mM MOPS pH 7.5, 0.1% Triton X100, 1 mM DTT, 0.25 mM NAD) 1 ul FAM-AG Uni2 (10 uM stock), 1 ul NED-GA Uni2 (10 uM stock), 1 ul mobility probe mix (1 uM stock), 0.25 ul ligase (40 units/ul), and 4.75 ul ddH20, thereby forming a reaction volume of 9 ul to which is added 1 ul of PCR amplification product. The reaction is cycled 30 times with a 95 C. melting step for 10 s, 60 C. annealing/ligation step for 1 minute. After the 30 cycles, reaction is held at 4 C.

All references cited herein are incorporated by reference for any purpose as if each was separately but expressly incorporated by reference.

Although the invention has been described with reference to particular embodiments, it will be appreciated that various changes and modifications may be made without departing from the scope and spirit of the invention.

What is claimed is:

1. A method for identifying a target nucleotide sequences in a sample comprising:
    performing a first ligation reaction, wherein a primary probe set is hybridized to the target and the primary probe set ligated together so as to form a first non-circular ligation products comprising a tag sequence that is not complementary to the target,
    performing a second ligation reaction, wherein a secondary probe set is hybridized to the tag sequence of the first non-circular ligation products and the secondary probe set ligated together so as to form a second non-circular ligation product,
    detecting the second non-circular ligation product, and identifying the target nucleotide sequence in the sample.

2. A method for identifying a target nucleotide sequence in a sample comprising;
    mixing the sample with a primary probe set, the primary probe set comprising
        (a) one or more first primary probes comprising a target specific portion, a target identifying portion, and a primer portion, wherein the one or more first primary probes differ from each other by at least one nucleotide in the target specific portion, and,
        (b) a second primary probe comprising a locus specific portion and a primer portion,
    wherein the one or more first probes are suitable for ligation with the second probe when hybridized adjacent to one another on the target nucleotide sequence, thereby forming a first ligase detection reaction mixture;
    subjecting the first ligase detection reaction mixture to one or more ligase detection reaction cycles to form one or more first non-circular ligation products, wherein each non-circular ligation product comprises the first primary probe ligated to the second primary probe;
    mixing the first ligation product with a secondary probe set, each secondary probe set comprising
        (a) one or more first secondary probes having a primer portion,
        (b) a second secondary probe having a target identifying portion,
    wherein the one or more first secondary probes are suitable for ligation with the second secondary probe when hybridized adjacent to one another on the first non-circular ligation product, thereby forming a second ligase detection reaction mixture;
    subjecting the second ligase detection reaction mixture to one or more ligase detection reaction cycles to form one or more second non-circular ligation products comprising the first probe of the secondary probe set ligated to the second probe of the secondary probe set;
    detecting the one or more second non-circular ligation products, and identifying the target nucleotide sequence in the sample.

3. The method according to claim 1 or 2, wherein the one or more first probes of the primary probe set further comprise the same target identifying portion and a different primer portion.

4. The method according to claim 1 or 2 further comprising amplification of the one or more first non-circular ligation products, amplification of the one or more second non-circular ligation products, or amplification of both the one or more first non-circular ligation products and the one or more second non-circular ligation products.

5. The method according to claim 1 or 2 further comprising;
    separating the one or more second non-circular ligation products from the second ligation detection reaction; and,
    identifying the one or more targets by the distinct primer portion, and target identifying portion of the second non-circular ligation products.

6. The method according to claim 5 wherein one or more probes of the secondary probe set further comprise a mobility modifying moiety, and wherein the separating further comprises a mobility-dependent analysis technique.

7. The method according to claim 6 wherein the mobility dependent analysis technique further comprises capillary electrophoresis.

8. The method according to claim 1 or 2 wherein one of the secondary probes further comprises a label.

9. The method according to claim 8 wherein the identity of the one or more targets is determined by hybridization of the target identifying portion of the second ligation product to an array.

10. The method according to claim 1 or 2 wherein the relative amounts of the one or more targets are compared between two or more samples.

11. The method according to claim 10 wherein the one or more targets further comprise expressed genes, the target nucleotide sequences of the two or more samples are in separate reactions, each sample being mixed with a primary probe set, the primary probe set comprising
   (a) one or more first primary probes comprising a target specific portion, a target identifying portion, and a primer portion,
   (b) one or more second primary probe comprising a locus specific portion and a primer portion,
   whereby the primer portion of the one or more first primary probe identifies the sample, and wherein the first and second probes are suitable for ligation when hybridized adjacent to one another on the target nucleotide sequence, thereby forming a first ligase detection reaction mixture;
   subjecting the first ligase detection reaction mixture to one or more ligase detection reaction cycles to form one or more first non-circular ligation products comprising
   (a) the primer portion and the target identifying portion of the first primary probe,
   (b) the target specific portion of the first primary probe and locus specific portion of the second primary probe ligated together, and,
   (c) the primer portion of the second primary probe;
   mixing the first ligation product with a secondary probe set, each secondary probe set comprising
   (a) a first secondary probe having a primer portion,
   (b) a second secondary probe having a target identifying portion,
   wherein the first and second probes of the secondary probe set are suitable for ligation when hybridized adjacent to one another on the first ligation product, thereby forming a second ligase detection reaction mixture;
   subjecting the second ligase detection reaction mixture to one or more ligase detection reaction cycles to form one or more second non-circular ligation products comprising the first and second probes of the secondary probe set ligated together.

12. The method according to claim 11 wherein the expressed genes are first converted into cDNA.

13. The method according to claim 10, wherein mutation profiling is performed in tumor samples.

14. The method according to claim 1 or 2 wherein removal of unincorporated reaction components is achieved with affinity moiety pull-out.

15. The method according to claim 14 wherein the affinity moiety pull-out further comprises biotin-streptavidin.

16. The method according to claim 1 or 2, wherein removal of unincorporated reaction components is achieved with enzymatic degradation.

17. The method according to claim 1 or 2, wherein the targets are initially amplified by a whole genome amplification procedure.

18. The method according to claim 1 or 2, wherein the targets are initially amplified by a partial genome amplification procedure.

* * * * *

UNITED STATES PATENT AND TRADEMARK OFFICE
CERTIFICATE OF CORRECTION

PATENT NO. : 7,255,994 B2 Page 1 of 1
APPLICATION NO. : 10/866012
DATED : August 14, 2007
INVENTOR(S) : Kai Qin Lao It is certified that error appears in the above-identified patent and that said Letters Patent is hereby corrected as shown below:

Claim 1, Column 23, line 54, please replace "sequences" with --sequence--.

Claim 1, Column 23, line 59, please replace "products" with --product--.

Claim 1, Column 23, line 63, please replace "products" with --product--.

Signed and Sealed this

Seventh Day of October, 2008

JON W. DUDAS
*Director of the United States Patent and Trademark Office*